United States Patent [19]

Urist

[11] Patent Number: 4,795,804
[45] Date of Patent: Jan. 3, 1989

[54] BONE MORPHOGENETIC AGENTS

[75] Inventor: Marshall R. Urist, Pacific Palisades, Calif.

[73] Assignee: The Regents of the University of California, Berkeley, Calif.

[21] Appl. No.: 763,479

[22] Filed: Aug. 7, 1985

Related U.S. Application Data

[63] Continuation-in-part of Ser. No. 523,606, Aug. 16, 1983, Pat. No. 4,619,989, which is a continuation-in-part of Ser. No. 260,726, May 5, 1981, Pat. No. 4,455,256, which is a continuation of Ser. No. 174,906, Aug. 4, 1980, Pat. No. 4,294,753.

[51] Int. Cl.$^4$ .............. C07G 7/00; C09H 1/00; A23J 1/00
[52] U.S. Cl. .................... 530/350; 530/355; 530/356; 530/417; 530/840; 424/95
[58] Field of Search ............... 530/350, 417, 356, 355, 530/840; 424/95

[56] References Cited

U.S. PATENT DOCUMENTS

| | | | |
|---|---|---|---|
| 2,384,673 | 9/1945 | Greffie | 530/355 |
| 2,717,835 | 9/1955 | Brody | 426/607 |
| 3,539,549 | 11/1970 | Greenfield | 530/419 |
| 3,887,717 | 6/1975 | Pfeiffer et al. | 426/264 |
| 4,243,582 | 1/1981 | Spilburg et al. | 530/840 |
| 4,294,753 | 10/1981 | Urist | 530/395 |
| 4,394,370 | 7/1983 | Jefferies | 424/423 |
| 4,434,094 | 2/1984 | Seyedin et al. | 530/416 |
| 4,455,256 | 6/1984 | Urist | 530/350 |
| 4,638,050 | 1/1987 | Aoki et al. | 530/350 |

OTHER PUBLICATIONS

Lancet, May 2, 1981, pp. 959-962, Glowacki et al.
Proc. Nat. Acad. Sci. U.S.A., (1979), 76(4), pp. 1828-1832, Urist et al.
Urist, Science, 150, pp. 893-899, (1965).
Proc. Soc. Exptl. Biology & Med., 162:48-53, (1979), Urist et al.
Urist et al., 15(4), 269-286, (1974), Calcified Tissue Research.
Urist et al., Clin. Orthop. Rel. Res. 53,243-283, (1967).
Clin. Orth. Rel. Res. 154, (1981), pp. 291-295, Baver et al.
Cell, 28, 96-105 (1981), Termine et al.
Chemistry and Biology of Mineralized Connective Tissues, Arthur Veis Editor, Conover et al., 597-606, 1981.
Clin. Orth. Rel. Res. 162 (1982), 219-232, Urist et al.
J. Biol. Chem., Oct. 25, 1981, Termine et al., pp. 10403-10408.
Proc. Soc. Expt. Biol. & Med. 173, 194-199 (1983), Urist et al.
Science, 220, pp. 680-686, Urist et al., May 13, 1983.

*Primary Examiner*—Morton Foelak
*Assistant Examiner*—Nathan M. Nutter
*Attorney, Agent, or Firm*—Kenyon & Kenyon

[57] ABSTRACT

The production and isolation of bone morphogenetic peptide agents displaying the osteoinductive and immunoreactive activity of bone morphogenetic protein (BMP) and deriving from natural, synthetic or recombinant DNA sources, and said agents.

21 Claims, 2 Drawing Sheets

BONE MORPHOGENETIC AGENTS

This invention was made with Government support under Grant No. DE 02103-20 with the National Institutes of Health and the University of California. The Government has certain rights in this invention.

This application is a continuation-in-part application of copending application Ser. No. 523,606, filed Aug. 16, 1983 and now U.S. Pat. No. 4,619,989, which in turn is a continuation-in-part application of application Ser. No. 260,726, filed May 5, 1981, now U.S. Pat. No. 4,455,256, which in turn is a continuation application of application Ser. No. 174,906, filed Aug. 4, 1980, now U.S. Pat. No. 4,294,753.

FIELD OF INVENTION

This invention relates to bone morphogenetic agents which are peptides that cause bone tissue to form and/or grow. More particularly, the present invention relates to bone morphogenetic peptides comprising at least an active portion of the osteoinductive and immunoreactive domain of the bone morphogenetic protein molecule, said peptide agents obtained from whatever source, including natural, synthetic or recombinant DNA sources, and their production, isolation, amino acid sequence and use.

BACKGROUND OF THE INVENTION

It has been demonstrated by the applicant that demineralized bone matrix induces new bone formation when inplanted in soft tissue. Freshly excised bone, demineralized in cold dilute HCl for 48 hours and implanted in brain, muscle subcutis, and bone defects, induces differentiation of postfetal mesenchymal-type perivascular connective tissue cells into cartilage and bone (Urist, M. R., *Science*, 150: 893–899, 1965). The process is generally designated as matrix induced bone formation. Further, the inductive principle has been discovered and extracted; it is a material designated bone morphogenetic protein (BMP). Reference is made to U.S. Pat. Nos. 4,294,753; 4,455,256; and application Ser. No. 523,606, filed Aug. 16, 1983 and now U.S. Pat. No. 4,619,989. See also: Urist, M. R., et al., *Proc. Soc. Exp. Biol. Med.*, 173: 194–199, 1983; and, Urist, M.R., et al., *Proc. Natl. Acad. Sci.* (USA) 81: 371–375, 1984. These patents, application and references are incorporated herein by reference.

It is believed that BMP transforms tissue cells into osteoblasts, cells that manufacture bone. Hypothetically, the process is classified as phenotypic transformation and the BMP is a paracrine molecule. As distinguished from malignant transformation by a carcinogen, phenotypic transformation is a self-limited host-regulated development process. During a process that replicates normal human fetal development, BMP-induced osteoblasts to form cartilage, which, over a period of several months, evolved into solid bone. The use of BMP implants by physicians offers considerable advantages over traditional bone graft operations. The list of present and potential uses for BMP includes almost every site in the human body: for use in replacing bone that has been destroyed by disease or accident; for use in treatment of scoliosis victims; for use in treatment of mal or misformed bone; for use in healing two edges of a fracture, and the like.

Currently, the process for isolation of BMP is relatively lengthy and expensive. Whereas milligram doses of BMP are required to induce bone formation in vivo, only microgram and picogram doses of hormones, vitamins and metabolites are needed to produce measureable biological reactions. One objective of the present invention was to identify and produce functional peptide segments of BMP that yield enhanced biological activity per unit of implanted bone morphogenetic material. Another objective was to create and produce biologically active peptides that are sequenced and then produced in quantity by direct biochemical synthesis from the constituent amino acids, for example, by the Merrifield method. Another objective of the present invention was to provide bone morphogenetic peptides that are sequenced and produced in quantity by expression of "genes" by recombinant DNA technology, or are used to construct nucleic acid screening probes for the isolation of the gene comprising the osteoinductive region of BMP for expression of bone morphogenetic peptides by recombinant DNA technology. Obtaining and characterizing peptide segments with bone morphogenetic activity is a key step in several commercially feasible processes to manufacture in quantity an efficient bone morphogenetic agent.

SUMMARY OF THE INVENTION

The present invention concerns bone morphogenetic peptide agents comprising at least an active portion of the osteoinductive and immunoreactive domain of the BMP molecule.

Bone morphogenetic peptides having a range of relative molecular weights ($M_r$) of about 4K to about 7K were produced by limited proteolysis of BMP from bovine bone and limited proteolysis of human bone matrix non-collagenous proteins. These bone morphogenetic peptide products were designated BMP-p and comprised osteoinductive and immunoreactive segments of the BMP molecule. Tables I and III contain the amino acid composition of two species of BMP-p, one (bovine) having a $M_r$ of about 4.1K and the other (human) having a $M_r$ of about 4.7K±0.3K. The N-terminal sequence of the first 36 amino acids of purified human BMP-p having a $M_r$ of about 4.7K±0.3K is given in Table IV.

Bone morphogenetic agents that comprise osteoinductive and immunoreactive domains of natural BMP molecules are prepared using the amino acid sequence of BMP-p, such as is given in Table IV, by conventional peptide synthesis procedures, e.g., the Merrifield method.

The full or partial amino acid sequence of BMP-p or of Table IV is employed by one skilled in the art of genetic engineering to synthesize DNA sequences which code on expression for bone morphogenetic peptides, or to synthesize DNA sequences which can be used as screening probes to isolate genes coding for the osteoinductive and/or immunoreactive regions of BMP. The synthetic DNA or the natural gene is inserted into a recombinant vehicle which is introduced into an appropriate host and expresses a bone morphogenetic peptide comprising an amino acid sequence substantially homologous with the amino acid sequence of Table IV. Bone morphogenetic peptides produced by these methods comprise osteoinductive and immunoreactive domains of BMP discovered and isolated by the applicant as described in U.S. Pat. Nos. 4,294,753; 4,455,256; and pending application Ser. No. 523,606, filed Aug. 16, 1983.

This invention also provides for the use of bone morphogenetic agents comprising osteoinductive and immunoreactive domain of BMP to induce cartilage and/or bone formation in animals and humans capable of benefiting from such induction.

This invention further provides a process for the production and purification of bone morphogenetic peptides from limited pepsin or trypsin proteolysis of bone morphogenetic protein (BMP). The bovine BMP-p and human BMP-p generated by limited proteolysis were isolated by any of one or more of: sequential differential precipitation, gel filtration, hydroxyapatite (HA) chromatography, and high pressure liquid chromatography (HPLC). The smallest functional unit of the bovine BMP-p segments isolated by high pressure liquid chromatography (HPLC) had a $M_r$ of about 4.1K. The $M_r$ of the smallest active human BMP-p isolated at this time was about $4.7K \pm 0.3K$.

DETAILED DESCRIPTION OF INVENTION

Figure 1:
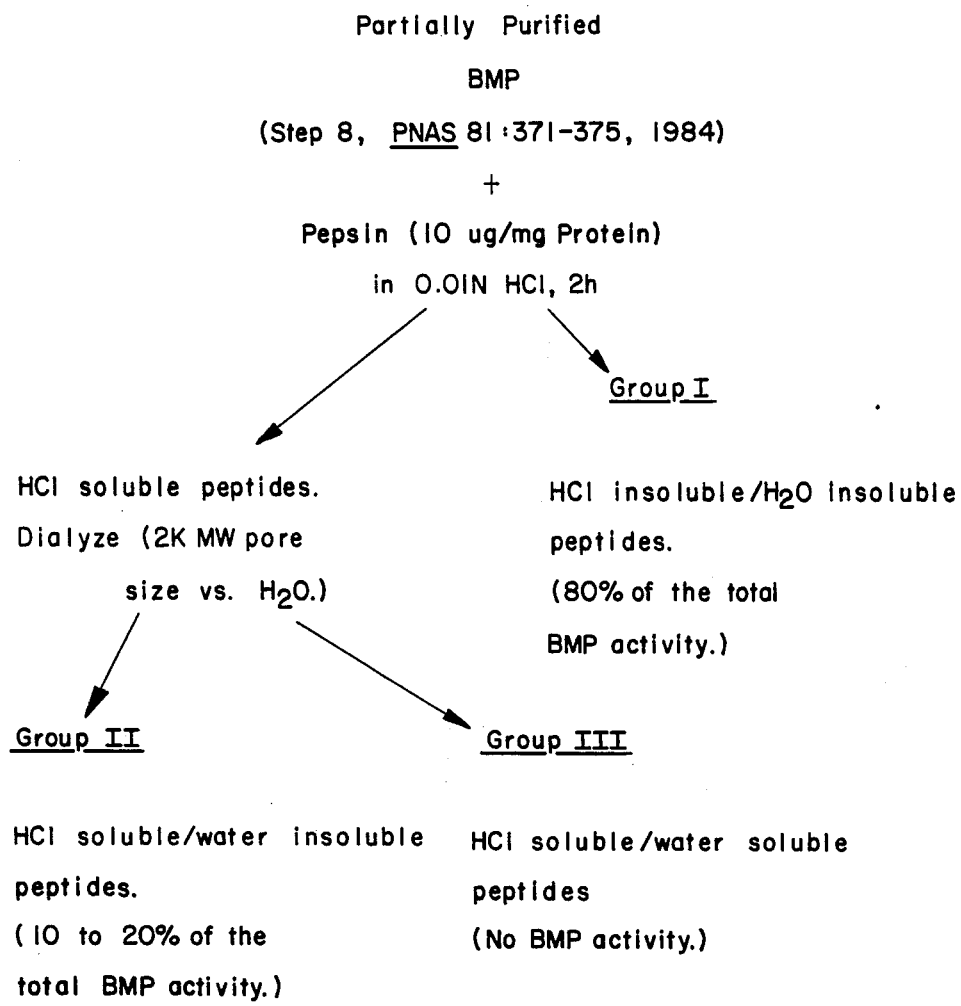
FIG. 1 depicts the steps of pepsin limited proteolysis of bovine BMP and the resultant products.

There are numerous examples of the role of proteases in biological systems, i.e., generation of hormones, activation of enzymes, assembly of fibrils, blood coagulation, etc. See, Neurath, H. (1980) in *Protein Folding*, Edited by K. Jaenick, Elservier Biomedical Press, New York, N.Y. pp. 501–524. Neither the inactive precursor nor the cell membrane receptors of either BMP or BMP-p are known.

Without intending to be limited by theory, it is thought that in vivo limited proteolysis of BMP occurs by the action of intracellular proteinases on BMP en route to formation of a nucleosome, and BMP induced DNA differentiation. According to this theory the BMP molecule is constructed of domains, hinges and fringes, with the active domain of the BMP molecule srrrounding a hydrophobic core that is inaccessible to limited proteolysis, and the structure of BMP is reduced and rearranged to generate smaller core peptides with the same or enhanced biological activity. Based on this hypothesis, experiments were undertaken to generate osteoinductive peptide fragments in vitro by means of limited proteolysis.

As more particularly described in Examples I, II and III below, bovine and human BMP were partially purified and subjected to limited pepsin or trypsin proteolysis. A group of osteoinductive and immunoreactive peptides were generated having a $M_r$ of about 4K to about 7K. These products are called bone morphogenetic peptides, and designated BMP-p. Sources other than bovine or human BMP are employed equally as well.

The observation is that the kinetics of pepsin proteolysis includes a rate limiting step during which hydrolysis is biphasic. In phase I, pepsin cleaves the fringes and hinges of the BMP molecule, sparing the active domain. Hydrolysis accelerates in phase II to rapidly degrade BMP-p. In individual batches, the densest population of BMP-p molecules reflects cleavage at various bonds among the hinges and fringes of the BMP molecule, sparing the active domain, with statistically most frequent $M_r$ of $5.3K \pm 1.0K$, and ranging from 4K to 7K.

Example I details the method of production and isolation of novel bone morphogenetic peptides (BMP-p) from bovine BMP. Example II details the method of production and isolation of BMP-p from human BMP.

In Example I, a 0.5M $CaCl_2$ –6M urea inorganic solvent mixture was used for the initial extraction of BMP from bovine bone. Urea was initially selected to avoid the relatively high expense of using guanidine hydrochloride (GuHCl) on batches of bones large enough to prepare significant quantities of BMP. Whenever urea was used, the N-terminal amino acids of BMP and BMP-p proved to be blocked, possibly by a firm isocyanate bond, and attempts to determine the N-terminal amino acid sequence of BMP and BMP-p by automated Edman degradation were unsuccessful. Since N-terminal blocking groups in proteins are usually not removable without degrading the protein, it was desirable to obtain BMP and BMP-p that could be sequenced. This became possible once it was discovered that BMP extracted with GuHCl contained an unblocked N-terminal amino acid.

Example II details the use of a high purity grade GuHCl in place of the urea employed in Example I; and the production of BMP and BMP-p with an unblocked N-terminal amino acid.

The BMP-p generated by limited pepsin proteolysis or trypsin proteolysis of human or bovine BMP was isolated by means of a combination of sequential differential precipitation, gel filtration, hydroxyapatite chromatography, and high pressure liquid chromatography. Various biologically-functional BMP-p species were characterized by $M_r$, immunoreactivity with BMP antibody, isoelectric focusing, amino acid composition analysis, and/or amino acid sequencing.

The sequence of the first thirty-six amino acids of the N-terminal segment of human BMP-p has been determined.

EXAMPLE I

Bovine bone morphogenetic protein (bBMP) was purified or partially purified from bovine bone by methods described in detail in the previously cited patents, publications, and copending application.

The purification process steps comprised: demineralizing bone tissue; treating the demineralized bone tissue under aqueous conditions with a water soluble neutral salt and a solubilizing agent for the BMP, the agent being selected from the group consisting of urea and guanidine, and thereby transforming the bone collagen to gelatine and extracting BMP into the solution of solubilizing agent; and separating the solubilizing agent and neutral salt from the solution, thereby precipitating BMP in the aqueous medium. In the present Example I, urea was used.

Purified BMP and partially purified BMP yield the same bone morphogenetic peptide products upon limited pepsin proteolysis as described below in detail for partially purified BMP.

Referring to the drawing, FIG. 1 depicts the steps of pepsin limited proteolysis of bovine BMP. One gram of the partially purified BMP (See Table 1, step 8, Urist et al. 1984) was digested for 2 hours at 37° C. in 2 liters of 0.01N HCl containing 10 μg pepsin (Sigma Co., St. Louis, Mo.) per mg. protein.

The partially purified BMP starting material comprised an assortment of about 15 proteins with $M_r$ ranging from 2.5K to 90K. After incubation in pepsin for 2 hours, proteins in the $M_r$ range from 30K to 90K were hydrolyzed and the peptide products of the limited pepsin treatment were separated into 3 groups:
Group I—HCl insoluble/water insoluble
Group II—HCl soluble/water insoluble
Group III—HCl soluble/water soluble
See FIG. 1.

When partially purified bovine BMP was incubated in 0.01N HCl for 2 hours in 2, 5, and 10 μg pepsin per mg of protein (enzyme to protein ratio 1:100), the HCl soluble/water insoluble components of the supernatant consistently induced bone formation. Other ratios (1:200 and 1:500) failed to produce this separation.

Initially, the pepsin cleaved peptide products were separated into HCl soluble (Group II and III) and HCl insoluble (Group I) parts. The Group I (HCl insoluble) peptide products were separated from the HCl soluble products (Groups I and III) by centrifugation at 50,000 g, washed 3× in 1 liter of cold deionized water, and collected by lyophilization.

The HCl soluble (II and III) peptides were separated by dialysis against deionized water (3×), until formation of a water insoluble precipitate was complete. This precipitate (Group II) was separated from the supernatant (Group III) by centrifugation at 50,000 g for 1 hour, and by washing 3× in cold water. Group II and III were lyophilized separately.

As described below these three groups of peptides produced by limited pepsin proteolysis were further fractionated, characterized by $M_r$, and bioassayed in vivo or in vitro.

Molecular weight ($M_r$) determinations were made by SDS-PAGE acrylamide gel electrophoresis. Lyophilized fractions were solubilized by incubation for 24 hours in 0.06 M Tris-HCl (pH 6.8) containing 2 M urea and 0.2% SDS. Five microliters (2.5% mg/ml) of each sample were applied to a 12.6% gel with a 3% stacking gel and were electrophoresed at 25 mA. The gels were stained with 0.25% Coomassie brilliant blue R-250 in methanol/acetic acid/$H_2O$ (5:1:5). The molecular weights were determined by using protein standards (Pharmacia), with a range of $M_r$ 94,000–14,000 and by peptide standards (Pharmacia) with a range of $M_r$ 17,200–1,600. The relative molecular mass ($M_r$) was calculated by plotting the logarithm of molecular weight versus distance of migration of 6 standard peptides relative to the distance of the unknown. (Swank and Munkres, 1971, Annal. Biochem. 39: 462.)

Bone morphogenetic activity was determined by implantation of lyophilized partially purified peptides and/or chromatographic fractions of peptides in the hindquarter muscles of Swiss-Webster strain mice. For controls, samples of the $M_r$ 38,000, 24,000, 15,000, 12,000, 4,000, 8,500, 3,000 and 2,500 products of pepsin proteolysis were implanted in the contralateral hindquarter muscle pouches.

The quantity of new bone was measured by correlated observations on roentgenograms, excised wet ossicle weights, histological sections, histomorphometric data, and $^{45}Ca$ uptake by calcified new bone. The histomorphimetry was performed on roentgenograms of histologically valid deposits of bone using the random point analysis method with the following formula:

$$\frac{\text{Points on radio-opaque bone} \times 100}{\text{Points on quadracepts muscle compartment}} = \% \text{ BMP-induced bone formation}$$

Bone morphogenetic activity was also assayed in tissue cultures. BMP was added to a CMRL (GIBCO) culture medium. The inductive activity per 0.1 to 1.0 mg of partially purified polypeptides was measured by counting the number of cartilage cells per low power field. Purified BMP was assayed in tissue cultures of 10 HPLC fractions, 10 mg/ml in triplicate by the method of Sato and Urist (1984), Clin. Orthop. 184: 180–187.

Figure 2:
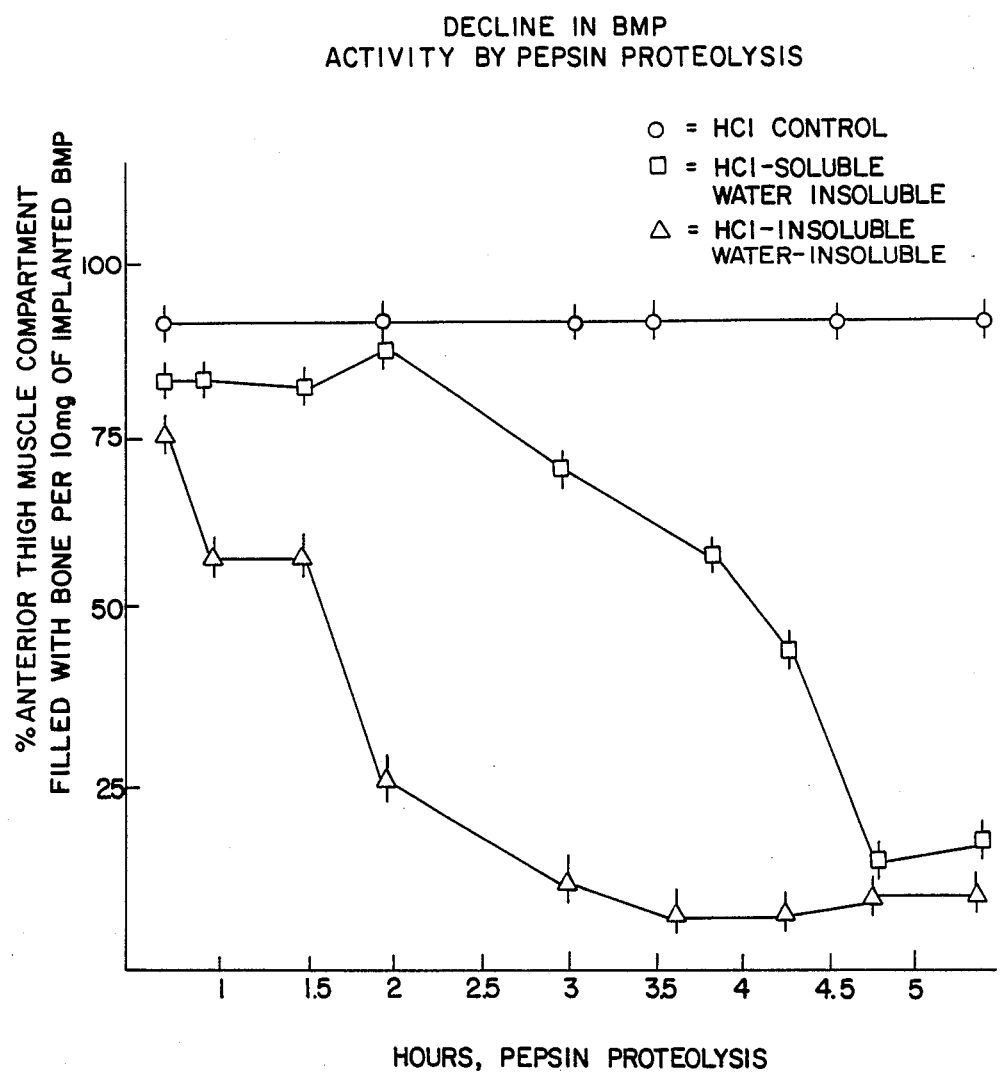
FIG. 2 depicts the decline in BMP activity over time of pepsin proteolysis.

Under the conditions specified, nearly all of the BMP activity was recovered and accounted for by the sum of the activities of Group I (78%) and Group II (22%). Group III peptides had no BMP activity and consequently were not isolated or further characterized. 16 As shown in FIG. 2, the products of proteolysis formed through about the first 2 hours of incubation maintained high BMP activity. Between 2 and 3 hours the sum of the HCl soluble and HCl insoluble products returned BMP activity almost as high as the partially purified BMP starting material. It was not until about 4 hours or more of incubation that the total BMP activity fell below about 50%.

The partially purified BMP starting material consisted of an assortment of about 15 proteins with an $M_r$ range from 2.5K to 90K. After incubation in pepsin for 2 hours, proteins in the $M_r$ range of 30K to 90K were hydrolyzed. The remaining polypeptides were partially digested peptides or spared peptides in the $M_r$ range of 2.5K to 30K. Although the quantity of induced bone formation was about 4 times greater in implants of HCl insoluble than soluble groups, the SDS Page patterns were equally cleared of proteins with $M_r$ greater than 30K, and the individual components were about the same in number.

Group I and II peptides were further fractionated as described below, and the bone inducing activity of both groups was always associated with peptides with $M_r$ less than 7K and greater than 3K.

Lyophilized Group II products were weighed and 0.7 g were redissolved in 0.05M phosphate buffer, pH 6.8 in 6M urea. The buffered solution was applied to a Sephacryl S-200 column (5 cm×95 cm) with downward flow regulated by a peristaltic pump and collected in 5 fractions. Two fractions with $M_r$ greater than 30,000 were pooled, dialyzed against water, and relyophilized for bioassay of new bone formation induced per mg of implanted protein. Three fractions with $M_r$ proteins less than 30,000 were pooled and similarly prepared. The proteins with $M_r$ less than 30,000 were further fractionated by hydroxyapatite (HA) chromatography, as follows. An 80 mg sample was applied to HA columns (2.5×40 cm) and eluted along a stepwise gradient of concentrations of 0.01 to 0.05, 0.05 to 0.2., 0.2 to 0.5M phosphate buffer in 6M urea. The proteins were collected in 9 fractions, examined by SDS gel electrophoresis, desalted in sacs with a pore size of 2,000 molecular weight by dialysis against water, lyophilized and implanted for BMP activity.

Peptides having $M_r$ less than 10K were subfractionated using Sephadex G-50 (ultrafine) molecular sieve chromatography. Samples of freeze-dried peptides were dissolved in 0.01M sodium phosphate (pH 7.0) containing 6M urea and charged to a column (1.5×100 cm) equilibrated in the same buffer. Fractions of approximately 20 ml each were collected, combined within each peak, dialyzed exhaustively against cold, deionized water and lyophilized. The resulting fractions were analyzed by SDS-PAGE peptide gels by the methods of Swank & Munkres, (1971).

Group I lyophilized products were dissolved in 100 ml of 6M urea and purified by sequential HA chromatography and G-50 gel filtration by the above described procedure.

Further purification of the peptides isolated by HA chromatography was accomplished by HPLC by methods previously described (Urist et al., 1984) and detailed below in Example II. Both HCl insoluble and HCl soluble groups of pepsin cleaved peptides yielded the $M_r$ 4K to 7K bBMP-p, including a large population of $M_r$ 5.6K±1.5K molecules, the smallest of which had an $M_r$ of about 4.1K.

The group II products of pepsin digestion that were fractionated first by Sephacryl S-200 gel filtration and then by HA chromatography yielded a broad spectrum of proteins and peptides. Approximately 95% of the products which had a $M_r$ less than 3K had no BMP activity. Nearly all of the bone inductive activity consisted of proteins and peptides in the $M_r$ range of 2.5K to 30K. Slab gel preparative electrophoresis preparations were made of HA chromatographic fractions and cuts were made from the areas of peptides in the $M_r$ range 4K to 7K, and in the $M_r$ range 2.K to 3K. The peptides in the gel slices were eluted with 6M urea, and reelectrophoresed. The combination of protein and peptide standards validated the assigned $M_r$ of the peptides in the range of about 4K to about 7K. Only the components in this range induced cartilage formation in vitro and bone formation in vivo. The peptides in the $M_r$ range 2K to 3K or lower (isolated by HA chromatography) did not induce bone formation.

HA chromatography of the Group I products of pepsin digestion yielded the same constituents (in somewhat different proportions) as obtained by HA chromatography of the Group II products discussed above. Peptide fractions with $M_r$ range 4K to 7K were eluted with 0.15 to 0.25M concentrations of phosphate ion, and found to induce bone formation. Peptides eluted at higher phosphate in concentrations had a $M_r$ of 1K to 2.5K and did not induce bone formation.

By means of Sephadex G-50 gel filtration chromatagraphy, the fractions with high BMP activity were resolved into 9 subfractions. Only one subfraction, further purified by HPLC and consisting of a peptide with a $M_r$ of about 4.1K, induced bone formation.

Biologically active fractions obtained by either G-50 or HA chromatography were separated into 10 subfractions with the aid of a reverse phase HPLC column (Urist et al., 1984). All 10 were bio-assayed in tissue cultures of connective tissue outgrowths of muscle. The subfraction containing peptide with an $M_r$ of 4.1K induced differentiation of cartilage. The quantity of cartilage varied from 2 to 9% of the total area of tissue in 6 serial sections of the culture. The nine other subfractions with components of higher and lower $M_r$ failed to induce cartilage cell differentiation in 27 other cultures prepared under identical conditions.

The pI of $M_r$ 4K to 7K peptides isolated by HA chromatography and HPLC was determined by isoelectric focusing by the method of Righetti and Drysdale in *Isoelectric Focusing*, Amsterdam, North Holland, Publ. Co., 1976, using a micropH probe (Microelectrodes, Inc.) for pH measurements on the cold gels (5% polyacrylamide and 2% ampholyte). Focusing was at 10 W at 2° C. for 3.5 hours. The pI is about 3.9.

Amino acid analysis was performed on an amino acid analyzer (Modified Beckman 121). Cystine and half cystine analysis was performed following performic acid oxidation. Table 1 presents the amino acid composition of the bovine BMP-p 4.1K peptide. The composition is characteristic of a composite of acidic polypeptides.

TABLE I

AMINO ACID ANALYSIS OF BOVINE BMP-p OF $M_r$ 4.1K ± 1.5K

| Amino Acid | nMoles | Mole % | Res/41 Res | Putative Residues |
|---|---|---|---|---|
| Lysine | 5.28 | 5.26 | 2.16 | (2) |
| Histidine | 2.96 | 2.95 | 1.21 | (1) |
| Arginine | 5.66 | 5.64 | 2.31 | (2) |
| Aspartic Acid | 13.01 | 12.97 | 5.32 | (5) |
| Threonin | 3.93 | 3.92 | 1.61 | (2) |
| Serine (corr. by 7.5%) | 4.68 | 4.67 | 1.91 | (2) |
| Glutamic Acid | 17.98 | 17.93 | 7.35 | (7) |
| Proline | 6.57 | 6.55 | 2.69 | (3) |
| Glycine | 5.82 | 5.80 | 2.34 | (2) |
| Alanine | 6.08 | 6.06 | 2.48 | (2-3) |
| ½ Cystine (Cysteic Acid) | 5.12 | 5.10 | 2.09 | (2) |
| Valine | 4.92 | 4.91 | 2.01 | (2) |
| Methionine | (0.94) | — | (0.38) | — |
| Isoleucine | 3.39 | 3.38 | 1.39 | (1-2) |
| Leucine | 6.88 | 6.86 | 2.81 | (3) |
| Tyrosine | 4.78 | 4.77 | 1.96 | (2) |
| Phenylalanine | 3.24 | 3.23 | 1.32 | (1-2) |
| | 100.30 | 100.00 | | 39-42 + Trp |

The $M_r$ 5.6K±1.5K group of peptides, and the $M_r$ 4.1K peptide were further purified by hydrophobic column chromatography, and analysed in the gas/liquid phase protein sequenator (Hewick, et al., 1981, *J. Biol. Chem.* 256: 1990.) The $M_r$ 4.1K BMP-p product of pepsin limited proteolysis had a blocked N-terminus, presumably the same as that of the $M_r$ 18.5K BMP from which it was derived.

Bovine BMP-p was tested for immunologic activity by means of the dot ELISA (Hawkes, et al., *Am. Biochem.* 119: 142–147, 1982) and found to cross react with mouse anti-bovine BMP ($M_r$ 18,500). Thus the immunoreactive and bioactive segments of bBMP-p ($M_r$ 4.1K) and bBMP (18.5K) appeared to be identical.

Ultrafiltration using $M_r$ 10K pore size has also been used to separate digested high from low $M_r$ peptides of Group I and II components.

From 120 implants of (1 to 10 mg samples) and ten 15 mg samples of partially purified BMP-p (assayed in triplicate) the percentages of the quadraceps compartment occupied by induced bone formation were calculated. The partially purified BMP displaced 50 to 90% of the quadracepts. The 0.01N HCl soluble/water insoluble products of limited pepsin proteolysis, Group II, displaced 20 to 75%; 0.01N HCl insoluble/water insoluble, Group I, 50 to 84%; 0.01 N HCl soluble/water soluble, Group III, 0%. The volume of the deposit was directly proportion to the doses in the range of 1 to 10 mg. Doses larger than 10 mg were found to produce more bone than the quadracepts compartment could contain and caused the deposits to grow across the pelvis into the contralateral limb.

Implants of 5 mg of partially purified BMP-p ($M_r$ 5.6K+155K) derived from either Group I or II, isolated by sequential HA chromatography and S-200 or G-50 gel filtration induced formation of bone deposits occupying 32% of the volume of the quadraceps compartment. The wet weight of a deposit of the volume of histologically valid bone dissected free of muscle tissue was about 200 mg.

Purified $M_r$ 4.1K BMP-p, isolated by HPLC, induced differentiation of cartilage in tissue culture and represented the smallest unit of polypeptide structure with biologic activity.

EXAMPLE II

By the mechanism of pepsin limited proteolysis of human BMP (hBMP), a group of peptides were generated having $M_r$ of 4K to 7K and the osteoinductive and immunoreactive properties of BMP.

Peptides having an $M_r$ of 4K to 7k were separated from higher and lower $M_r$ polypeptides by S-200 gel filtration of a 4M GuHCl solution of the products of pepsin proteolysis. All of the osteoinductive activity was concentrated in the peptides with $M_r$ of 4K to 7k. None was found in fractions with $M_r$ greater than 7K or lower than 3K. By means of G-50 filtration of these fractions, a group of peptides with a $M_r$ of 5.5K±0.8K was isolated. This group also induced differentiation of cartilage and bone in a muscle pouch in the mouse thigh.

Further purification of the G-50 isolated hBMP-p with HPLC produced peptides with $M_r$ of 4.7K±0.3K. Different biochemists working on three separate batches of about 1.5 kilos each of fresh wet bone, produced hBMP-p having $M_r$ of 4.7K, 5.0K, and 4.4K. The 4.7K human BMP-p induced cartilage in tissue cultures.

The materials and methods were as follows:

Five kg of human cortical bone were excised at autopsies of 22 to 51 year old men within 12 hours after accidental death following the guidelines of the Anatomical Gifts Act of California. The diaphyseal cortical bone was extensively washed, mechanically demarrowed, defatted in 1:1 chloroform-methanol, frozen in liquid N2, and ground into 0.5 $mm^3$ particles in a Wiley Mill. The ground bone particles were demineralized in 0.6N HCl for 48 hours, washed, and the hBMP extracted with 4M guanidine HCl (GuHCl) containing sulfhydryl group enzyme inhibitors and differential precipitation in 1.5M GuHCl containing 5 mmoles/l of N-ethyl maleiamide. Ostenonectin was removed with 0.2% Triton X-100, and matrix gla protein (MGP) by ultrafiltration through a hollow fiber cartidge HlP10-8, approximate cut-off $M_r$ 10,000. One gram of the 1.5M GuHCl insoluble proteins was digested for 2 hours in a solution of pepsin (Sigma Co, St. Louis) 10 μg/mg (enzyme to protein ratio 1:100) in 0.01N HCl at 37° C. The pepsin-cleaved HCl insoluble/water insoluble and HCl soluble/water insoluble fractions were separated from the HCl soluble/water soluble proteins by centrifugation at 50,000 g. for one hour. Hydrolysis was terminated by dialysis by raising the the pH to 7.0 with 0.01M NaOH and by dialysis against cold water in Spectrophor tubing, (pore size cutoff, mol. wt. 2,000 Spectrum Co. Los Angeles, Calif.).

The 0.01N HCl soluble products were lyophilized, weighed, and 0.7 g were redissolved in 0.05M phosphate buffer, ph 6.8 in 4M GuHCl. The buffered solution was applied to a Sephacryl S-200 column (5 cm×95 cm) with downward flow regulated by a peristaltic pump and collected in 5 fractions. Two fractions with $M_r$ greater than 30,000 were pooled, dialyzed against water, and relyophilized for bioassay of new bone formation induced per mg of implanted protein. Three fractions with $M_r$ less than 30,000 were pooled and similiarly prepared. Eighty mg samples of the proteins with $M_r$ less than 30,000 were applied to a hydroxyapatite column (HA) (2.5×4.0 cm) and eluted along a stepwise gradient of concentrations of 0.01 to 0.05, 0.05 to 0.2, 0.2 to 0.5M phosphate buffer. The proteins were collected in 9 fractions, examined by SDS gel electrophoresis, desalted in sacs (pore size, mol. wt., 2,000) by dialysis against cold water, lyophilzied and implanted for BMP activity.

Peptides ($M_r$ less than 10K) were subfractionated using Sephadex G-50 Ultrafine molecular sieve chromatography. Samples of freeze-dried peptides were dissolved in 0.01M sodium phosphate (pH 7.0) containing 4M GuHCl and charged to a column (1.5×100 cm) equilibrated in the same buffer. Fractions of approximately 20 ml each were collected, combined within each peak, dialyzed exhaustively against cold, deionized water and lyophilized. The resulting fractions were analyzed by SDS-PAGE peptide gels by the methods of Swank & Munkres (1971).

The pepsin cleaved 0.01N HCl insoluble, water insoluble products remaining from the two hour limited pepsin proteolysis were separated from the 0.01N HCl soluble products by centrifugation at 50,000 g, washed 3× in 1 liter of cold deionized water, and collected by lyophilization. The lyophilized proteins and peptides were dissolved in 4M GuHCl and similarly fractionated by the above described procedures. Matrix gla protein (MGP) persisting insoluble aggregates containing high BMP activity, was removed by solubilization in 4 M GuHCl and ultrafilitration.

Reverse phase high performance liquid chromatography (HPCL) was performed on $M_r$ 5,500±1,000 protein fractions isolated by Sephadex G-50 chromatography. These fractions were dissolved in 4M guandinium hydrochloride buffered with 0.01 M phosphate (pH 7.2). After centrifugation through a nylon 66 membrane (to eliminate any vestige of undissolved protein), the sample was charged to a Vydac (C4) column (4.6 mm×25 cm) (Co, City) and eluted with a gradient of 0.1% trifluoracetic acid (TFA) in water and 0.1% TFA in acetonitrile (AN). The gradient was started at 20% AN and continued to 35% AN in 15 minutes (1% per minute). From 35% AN to 50% AN was accomplished in 10 minutes after which the column was reequilibrated. The higher concentration of TFA served to effect better resolution of closely eluting materials and also allowed better correlation between analytical and preparative chromatographies. After appropriate fractions were collected, the TFA and AN were eliminated by vacuum centrifugation. The samples were recovered in a dry state by lyophilization.

For determination of $M_r$, protein fractions were examined by sodium dodecyl sulfate polyacrylamide slab gel electrophoresis (SDS PAGE). The lyophilized proteins were solubilized by incubation for 24 hours in 0.06M Tris-HCl (pH 6.8) containing 2M urea and 0.2% SDS. Five microliters (2.5 mg/ml) of each sample were applied to a 12.6% gel with a 3% stacking gel and were electrophoresed at 25 mA. The gels were stained with 0.25% Coomaissie brilliant blue R-250 in methanol/acetic acid/$H_2O$ (5:1:5). The molecular weights were determined by using protein standards (Pharmacia) with a range of $M_r$ 94,000–14,400 and by peptide standards (Pharmacia) with a range of $M_r$ 17,200–1,600. The relative molecular mass ($M_r$) was calculated by plotting the logarithm of molecular weight versus distance of migration of 6 standard peptides relative to the distance of the unknown. (Swank & Munkres).

The population density of human BMP-p molecules was concentrated in the region of $M_r$ of 5.5K±0.8K. Bovine BMP-p of Example I included molecules with $M_r$ as small as 4.1K±0.3K.

Bioassay of BMP-p for osteoinductive activity was determined by implantation of 128 lyophilized preparations in the hindquarter muscles of Swiss-Webster strain mice. For controls, 10 samples each of osteonectin ($M_r$ 38,000), $M_r$ 24,000, MGP ($M_r$ 14,000 to 15,000), and $M_r$ 12,000, 8,500, 4,000, 3,000, and 2,500 products of pepsin proteolysis were implanted in the contralateral hindquarter muscle pouches.

The quantity of new bone was measured by correlated observations on roentgenograms, excised wet ossicle weights, histological sections, histomorphometric data, and $^{45}Ca$ uptake by calcified new bone as described above in Example I. Histomorphometric data were obtained by random point analysis.

Human BMP-p was soluble in CMRL (GIBCO) culture medium containing 15% fetal calf serum, and assayed also in tissue cultures of 10 HPLC fractions, 10 μg/ml, in triplicate by the method of Sato and Urist.

Table II summarizes results of bioassay of osteoinductive proteins and peptides, including by-products of various stages of purification. Bone matrix non-collagenous proteins (separated by differential precipitation from solutions of GuHCl) had a low level of osteoinductive activity. Partial purification by HA chromatography increased the specific activity 25× as measured by histomorphometry and 950× by incorporation of $^{45}Ca$ into calcifying new bone. Further purification increased the quantity of induced bone formation in both parameters.

TABLE II
BIOASSAY OF PROTEINS COMPARED WITH PEPTIDES GENERATED BY LIMITED PEPSIN PROTEOLYSIS

| Components | Bone Histomorphometric mm²/mm² of muscles | $^{45}Ca$ uptake by calfifying new bone cpm/mg implanted protein |
|---|---|---|
| 1.5 M GuHCl Insoluble/water soluble non-collagenous proteins, 90 to 30K | 0.5 | 302 ± 104 |
| 38K Triton X-100 soluble proteins | 0 | 20 ± 09 |
| 34K CL-6B Isolated osteonectin | 0 | 25 ± 11 |
| 30 + 24 + 22K 1.5 M GuHCl Soluble proteins | 0 | 31 ± 11 |
| 24K Hydroxy apatite unbound protein | 0 | 26 ± 08 |
| 17.5K BMP + 15 + 14K gla Protein | 12.4 | 2660 ± 500 |
| 14K Bone gla Protein | 0 | 45 ± 10 |
| Pepsin generated 7 to 14K polypeptides | 28.5 | 3696 ± 980 |
| 5.5 ± 0.8K G-50 Isolated polypeptides | 13.0 | 2964 ± 608 |
| 4.7K HPLC Purified polypeptides | Cartilage in tissue cultures | N.D. |

The pI of peptides isolated by HA chromatography and HPLC was determined by isoelectric focusing by the method of Righetti and Drysdale (1976) using a micropH probe (Microelectrodes, Inc.) for pH measurements on the cold gels (5% polyacrylamide and 2% ampholyte). Focusing was at 10 W at 2° C. for 3.5 hours. The pI of the $M_r$ 4.7K peptide was about 7.1±0.1.

Amino acid analyses were performed on an amino acid analyzer (modified Beckman 121). Cystine and half cystine analysis was performed following performic acid oxidation. The composition was characteristic of a neutral peptide. The amino acid composition of the $M_r$ 4.7K peptide is presented in Table III.

TABLE III
AMINO ACID ANALYSIS OF $M_r$ 4.7K HUMAN BMP-p ISOLATED BY REVERSAL PHASE HPLC

| | nMoles; | nGrams | Mole %; | Residues | Putative Residues |
|---|---|---|---|---|---|
| Lys | 4.31 | 552.4 | 4.64 | 2.36 | (2) |
| His | 2.30 | 315.4 | 2.48 | 1.26 | (1) |
| Arg | 16.69 | 2606.6 | 17.97 | 9.12 | (9) |
| Asx | 7.63 | 878.1 | 8.22 | 4.17 | (4) |
| Thr | 0.85 | 85.9 | 0.92 | 0.47 | (0-1) |
| Ser (corr. by 10%) | 5.08 | 442.3 | 5.47 | 2.78 | (3) |
| Glu | 18.79 | 2426.0 | 20.23 | 10.27 | (10) |
| Pro | 7.54 | 732.2 | 8.12 | 4.12 | (4) |
| Gly | 2.16 | 123.2 | 2.33 | 1.18 | (1) |
| Ala | 6.24 | 443.5 | 6.72 | 3.41 | (3) |
| ½ Cys (Cysteic Acid) | 6.30 | 3.3 | 1.35 | 3.1 | (2) |
| Val | 4.18 | 414.4 | 4.50 | 2.28 | (2) |
| Met | 1.26 | 165.3 | 1.36 | 0.69 | (1) |
| Ile | 4.00 | 452.6 | 4.31 | 2.19 | (2) |
| Leu | 4.68 | 529.5 | 5.04 | 2.56 | (2-3) |
| Tyr | 5.32 | 868.1 | 5.73 | 2.81 | (3) |
| Phe | 1.83 | 269.3 | 1.97 | 1.00 | (1) |
| | 92.86 | 11,304.8* | 100.01 | | 50-52 + Trp |

*11,304.8 nGrams = 11.3 g; or 113 g in 1.0 ml (32% protein)

Amino acid sequences of the HPLC purified peptides were analyzed in the gas/liquid phase protein sequenator. The partial amino acid sequence of the N-terminal segment of HPLC purified human BMP-p is shown in Table IV.

The amino acid sequence of the first 15 residues of the N-terminal segment of hBMP-p was reproducible on 3 separate batches of bone. The sequence of residues 17 to 27 were determined with less certainty, and 28 to 36 with interesting inconsistencies that require special investigation.

TABLE IV
PARTIAL AMINO ACID SEQUENCE OF hBMP—p

|  | 1 | 2 | 3 | 4 | 5 |
|---|---|---|---|---|---|
|  | NH₂—ILE | —PRO | —GLN | —GLN | —ARG |
|  | 6 | 7 | 8 | 9 | 10 |
|  | —ARG | —TRP | —ARG | —ALA | —LYS |
|  | 11 | 12 | 13 | 14 | 15 |
|  | —VAL | —GLN | —ASN | —ARG | —ILE |

| | 16 | 17 | 18 | 19 | 20 |
|---|---|---|---|---|---|
| (Less certain than 1-15) | —(ALA?) | —ARG | —ASP | —SER | —TYR |
| | 21 | 22 | 23 | 24 | 25 |
| | —LYS | —PRO | —VAL | —HIS | —GLU |

| | 26 | 27 | 28 | 29 | 30 |
|---|---|---|---|---|---|
| | —LEU | —ASN | —ARG | —CYS | —ALA |
| (Less certain than 17-27) | 31 | 32 | 33 | 34 | 35 |
| | —ASP | —GLY | —TYR | —ARG | —LEU |
| | 36 | | | | |
| | —CYS— | | | | |

EXAMPLE III

Trypsin proteolysis of purified or partially purified BMP generated BMP-p. The trypsin derived BMP-p were purified, bio-assayed and characterized by the same methods that were reported for isolation of pepsin-derived BMP-p.

One g of crude partially purified BMP was digested for intervals of 15 min., 30 min., 1 hr. and 4 hrs. in solutions of trypsin (TPCK-treated, bovine pancrease, Sigma, St. Louis), 5 mg per g of total protein in 0.1M Tris pH 7.20 at 37° C. At the designated interval, hydrolysis was terminated by the addition of 1N HCl to produce a pH of 1.0. The solution was centrifuged at 20,000 rpm for 10 min. to separate the acid soluble from the acid insoluble precipitates. The precipitate was washed in cold water 3×. The acid soluble supernatant was transferred to Spectrapor tubing (pore size 2,000 MW, Spectrum, Co., Los Angeles), and dialyzed against ionized water (3×). A water insoluble precipitate that formed inside the sac was separated from the water soluble components by centrifugation at 50,000 g. for 1 hr., and by washing the precipitate 3× in deionized cold water. The water soluble supernatant and the washed precipitates were separately collected, lyophilized, and weighed.

The lyophilized products were weighed and redissolved in 0.05M phosphate buffer, pH 6.8 in 4M GuHCl for S-200 gel filtration. The solutions were applied to a Sephacryl S-200 column (5 cm x 95 cm) with downward flow regulated by a peristaltic pump and collected in 5 fractions. Two fractions with $M_r$ greater than 30,000 were pooled, dialyzed against water, and relyophilized for bioassay of new bone formation induced per mg of implanted protein. Three fractions with $M_r$ proteins less than 30,000, were pooled and similarly prepared.

The proteins with $M_r$ less than 30,000 were subfractionated using Sephadex G-50 (Ultrafine) molecular sieve chromatography. Samples of freeze-dried polypeptides were dissolved in 0.01M sodium phosphate (pH 7.0) containing 6M urea and charged to a column (1.5×100 cm) equilibrated in the same buffer. Fractions of approximately 20 ml each were collected, combined within each peak, dialyzed extensively against cold deionized water, and lyophilized. The resulting fractions were analyzed by SDS-PAGE peptide gels by the methods of Swank & Munkres.

Further purification of the polypeptides, isolated by G-50 gel filtration was accomplished by HPLC using a hydrophobic column (Ultrapore, reverse-phase Spherogel, Beckman).

Implants of crude partially purified BMP induced formation of cartilage and bone in mice. The deposits replaced approximately 4% of the volume of the quadriceps muscle compartment. Implants of the products of trypsinlimited proteolysis, both acid-insoluble and acid-soluble fractions, induced cartilage and bone tissue formations that filled the entire quadriceps compartment and sometimes even extended across the midline. The reaction to the acid insoluble/water soluble proteins produced formation of fibrous connective tissue only.

The deposits of bone induced by implants of products of limited trypsin proteolysis had the same structure as deposits produced by implants of BMP. The bone consisted of a shell of lamellar bone filled with bone marrow, and a core of woven bone containing inclusions of cartilage and chondro osteoid.

EXAMPLE IV

Bone morphogenetic agents are prepared by conventional chemical synthesis of peptides from constituent amino acids comprising the amino acid sequence (or substantially homologous equivalents) of BMP-p such as is given in Table IV. A method of chemical synthesis of peptides is the Merrifield method. Merrifield, R. B., *J. Am. Chem. Soc.*, 85:2194, 1963; Merrifield, R. B., *Science.* 150:178, 1965.

Such synthetic bone morphogenetic peptide agents comprise the osteoinductive and immunoreactive domain of natural BMP.

EXAMPLE V

By methods known to one skilled in the art of genetic engineering, synthetic DNA "genes" coding on expression for bone morphogenetic agents are constructed comprising the codon sequence for the amino acid sequence for BMP-p such as is given in Table IV. The required DNA sequence is determined from the amino acid sequence and the genetic code, and a "gene" is chemically synthesized and inserted into a recombinant DNA vector. The recombinant vector is introduced into a host cell, such as *E. coli.* in which it is replicated and expressed when the cell is cultured. During growth of the host cell in culture, the host cell machinery transcribes mRNA from the synthetic gene and translates it into bone morphogenetic peptide agents. Variables such as vector choice, host choice, position of the synthetic gene in the recombinant vector, etc., are manipulated to engineer in vivo cultures that are efficient factories for the production of bone morphogenetic peptide agents displaying the osteoinductive and immunoreactive activity of natural BMP or BMP-p.

For these methods available to one skilled in the art of genetic engineering, see for example, Maniatis, T., Fritsch, E. F., and Sambrook, J., (1982) *Molecular Cloning, A Laboratory Manual,* Cold Spring Harbor Laboratory, Cold Spring Harbor, N.Y.

EXAMPLE VI

By methods available to one skilled in the art of genetic engineering (see Maniatis et al. above), bone morphogenetic agents are produced by expressing cloned cDNA or cloned fragments of vertebrate DNA which comprise the codon sequence for part or all of the amino acid sequence for BMP-p given in Table IV.

Using known recombinant DNA techniques, fragments of a vertebrate genome or cDNA are inserted into vectors, and the recombinant vectors are introduced into host organisms. Novel radiolabelled nucleic acid probes of single stranded DNA or RNA comprising codons for some or all of the amino acid sequence for BMP-p given in Table IV are synthesized chemically. These probes (or the complementary strands of these specific nucleic acids) are used to screen host colonies for complimentary sequences and thereby to select recombinant clones with a DNA sequence comprising the osteoinductive and immunoreactive domain of BMP. Selected colonies are cultured and tested for the production of peptides that are osteoinductive or immunoreactive with anti-BMP antibody.

Alternatively, novel radiolabelled nucleic acid probes comprising codons for some or all of the amino acid sequence for BMP-p given in Table IV are used to identify and select by hybridization RNA, cDNA or fragments of vertebrate DNA that comprise codons for the osteoinductive region of BMP. Those selected are used to construct recombinant vectors for the production of bone morphogenetic agents in a host.

Although the instant disclosure sets forth all essential information in connection with the invention, the numerous publications cited herein may be of assistance in understanding the background of the invention and the state of the art. Accordingly, all of the publications cited are hereby incorporated by reference into the present disclosure.

It will be understood that this description and disclosure of the invention is intended to cover all changes and modifications of the invention which are within the spirit and scope of the invention. It is within the knowledge of the art to insert, delete or substitute amino acids within the amino acid sequence of a given BMP-p without substantially affecting the bone morphogenetic activity of the molecule. The invention is expressly stated to be broad enough to include intentional deletions, additions or substitutions. Furthermore, it is recognized that one skilled in the art could recombinantly produce such modified proteins.

What is claimed is:

1. A bone morphogenetic peptide having an amino acid sequence, said sequence selected from the group consisting of amino acid sequences of peptide fragments (BMP-p) having a relative molecular weight ($M_r$) of about 4K to about 7K and derived from proteolysis of bone morphogenetic protein (BMP), said peptide fragments being osteoinductive and immunoreactive with anti-BMP antibody.

2. A bone morphogenetic peptide of claim 1, wherein the BMP is human BMP.

3. A bone morphogenetic peptide of claim 2, wherein the relative molecular weight ($M_r$) is about 4.7K±0.3K.

4. A bone morphogenetic peptide of claims 1, 2 or 3 wherein the amino acid sequence contains the following amino acid sequence: -ILE - PRO - GLN - GLN - ARG - ARG - TRP - ARG - ALA - LYS - VAL - GLN - ASN - ARG - ILE-.

5. A bone morphogenentic peptide of claim 4, further including the following amino acid sequence: -ARG - ASP - SER - TYR - LYS - PRO - VAL - HIS - GLU - LEU - ASN-.

6. A bone morphogenetic peptide of claim 5, further including the following amino acid sequence: -ARG - CYS - ALA - ASP - GLY - TYR - ARG - LEU - CYS-.

7. A bone morphogenetic peptide of claim 1, wherein the BMP is bovine BMP.

8. A bone morphogenetic peptide of claim 7, wherein the relative molecular weight ($M_r$) is about 4.1K.

9. A bone morphogenetic peptide of claim 1, 2 or 3, wherein the limited proteolysis is pepsin limited proteolysis.

10. A bone morphogenetic peptide of claim 4, wherein the limited proteolysis is pepsin limited proteolysis.

11. A bone morphogenetic peptide of claim 1, 2 or 7, wherein the limited proteolysis is trypsin limited proteolysis.

12. A composition for inducing bone formation comprising a bone morphogenetic peptide selected from the group of bone morphogenetic peptides of claims 1, 2, 3, 7 or 8.

13. A composition for inducing bone formation comprising a bone morphogenetic peptide selected from the group of bone morphogenetic peptides of claim 4.

14. A composition for inducing bone formation comprising a bone morphogenetic peptide selected from the group of bone morphogenetic peptides of claims 9.

15. A composition for inducing bone formation comprising a bone morphogenetic peptide selected from the group of bone morphogenetic peptides of claims 10.

16. A composition for inducing bone formation comprising a bone morphogenetic peptide selected from the group of bone morphogenetic peptides of claims 11.

17. A method for inducing bone formation in vertebrates which comprises administering to said vertebrate in a pharmaceutically acceptable manner an effective amount of a composition according to claim 12.

18. A method for inducing bone formation in vertebrates which comprises adminstering to said vertebrate in a pharmaceutically acceptable manner an effective amount of a composition according to claim 13.

19. A method for inducing bone formation in vertebrates which comprises administering to said vertebrate in a pharmaceutically acceptable manner an effective amount of a composition according to claim 14.

20. A method for inducing bone formation in vertebrates which comprises administering to said vertebrate in a pharmaceutically acceptable manner an effective amount of a composition according to claim 15.

21. A method for inducing bone formation in vertebraes which comprises administering to said vertebrate in a pharamceutically acceptable manner an effective amount of a composition according to claim 16.

* * * * *